(12) United States Patent
Kwong

(10) Patent No.: US 8,986,200 B2
(45) Date of Patent: Mar. 24, 2015

(54) MEDICAL DEVICE

(75) Inventor: Tsong Yun Kwong, Middlesex (GB)

(73) Assignee: Medivention Limited, London (GB)

( * ) Notice: Subject to any disclaimer, the term of this patent is extended or adjusted under 35 U.S.C. 154(b) by 0 days.

(21) Appl. No.: 13/822,933

(22) PCT Filed: Sep. 15, 2011

(86) PCT No.: PCT/GB2011/051736
§ 371 (c)(1),
(2), (4) Date: Mar. 13, 2013

(87) PCT Pub. No.: WO2012/035351
PCT Pub. Date: Mar. 22, 2012

(65) Prior Publication Data
US 2013/0178707 A1    Jul. 11, 2013

(30) Foreign Application Priority Data

Sep. 15, 2010  (GB) .................................. 1015335.1
Apr. 27, 2011  (GB) .................................. 1107018.2

(51) Int. Cl.
*A61B 1/227* (2006.01)
*A61B 3/12* (2006.01)
*A61B 1/06* (2006.01)

(52) U.S. Cl.
CPC .............. *A61B 3/1208* (2013.01); *A61B 1/227* (2013.01); *A61B 3/1216* (2013.01); *A61B 1/06* (2013.01)
USPC ............ 600/200; 600/245; 600/246; 600/199

(58) Field of Classification Search
CPC ........ A61B 1/227; A61B 1/2275; A61B 3/00; A61B 3/12; A61B 3/1208
USPC ................................... 600/200, 245, 246, 199
See application file for complete search history.

(56) References Cited

U.S. PATENT DOCUMENTS 1,608,726 A * 11/1926 De Zeng ........................ 600/200
3,978,850 A *  9/1976 Moore et al. .................. 600/200
4,785,796 A * 11/1988 Mattson ........................ 600/200

FOREIGN PATENT DOCUMENTS

| DE | 4101780 A1 | 7/1992 |
| EP | 0641540 A1 | 3/1995 |
| WO | WO-2011042743 A2 | 4/2011 |

OTHER PUBLICATIONS

International Search Report dated Dec. 19, 2011; 5 pgs.

* cited by examiner

*Primary Examiner* — Eduardo C Robert
*Assistant Examiner* — Julianna N Harvey
(74) *Attorney, Agent, or Firm* — Gifford, Krass, Sprinkle, Anderson & Citkowski, P.C.

(57) ABSTRACT

A device forming a combination ophthalmoscope and otoscope, having a housing (4) supporting a light source (10) and a plurality of lenses (8, 9), the light source (10) defining an illumination light path (14) which illuminates in use a region of interest (15), the housing having an aperture (12) defining a viewing light path (13) along which the region of interest (15) can be viewed, the lenses (8, 9) being mounted on a support (1) relative to the housing (4) so as to be moveable relative to the housing (1) so as to allow selection of a lens from the plurality of lenses (8, 9) to be disposed in the viewing light path, and in which the plurality of lenses form an ophthalmoscopy set (8) comprising at least one ophthalmoscopy lens and an otoscopy set (9) comprising at least one otoscopy lens.

19 Claims, 3 Drawing Sheets

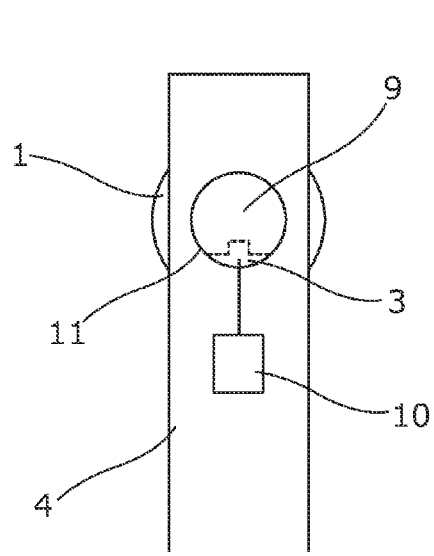
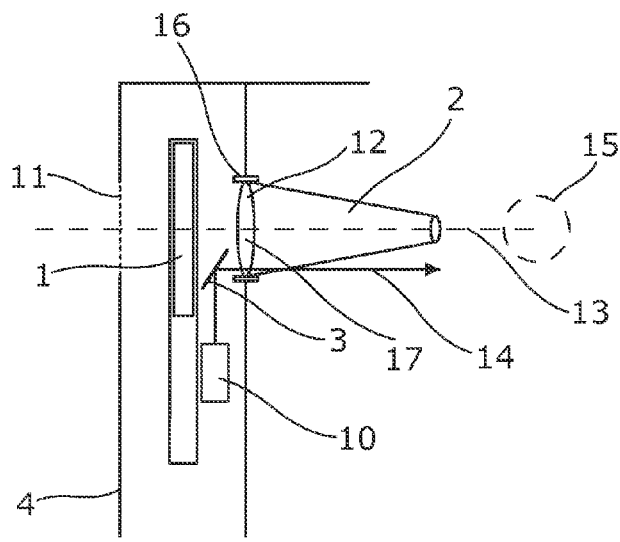
Fig. 1A        Fig. 1B
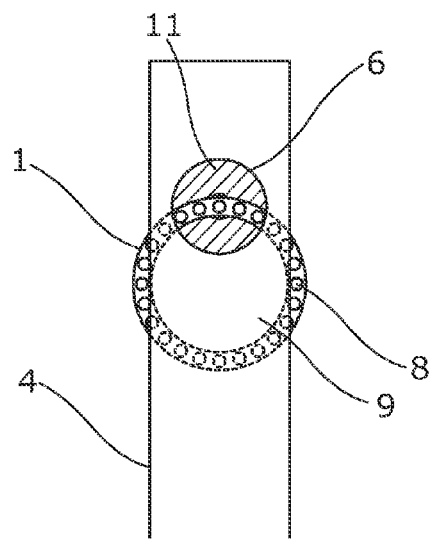
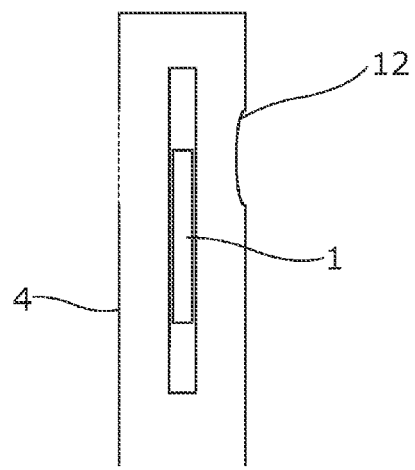
Fig. 1C        Fig. 1D

MEDICAL DEVICE

CROSS-REFERENCE TO RELATED APPLICATIONS

This application is the U.S. National Phase of PCT/GB2011/051736 filed Sep. 15, 2011, which claims priority of Great Britain Patent Applications 1015335.1 filed Sep. 15, 2010, and 1107018.2 filed Apr. 27, 2011.

This invention relates to a medical device being a combination ophthalmoscope and otoscope device.

During examination it is essential that a doctor has a range of instruments at his disposal to perform such examinations as neurological and ears, nose and throat (ENT). However this kit is often heavy and cumbersome and as a result doctors do not often perform a full physical examination on their patients. Even the most basic selection is expensive and has a mass of more than 1 kg. Very often, tools are unavailable or non-functioning leading to clinicians spending valuable time hunting down tools.

In particular, with an ophthalmoscope (used to examine the rear surface or retina of the eye and the pupils) and otoscope (used to examine the ear canal, and in particular the tympanic membrane), there is often one common battery shaft which can connect to interchangeable ophthalmoscope and otoscope heads. It can also be noted that illumination provided by the otoscope and ophthalmoscope can have general illumination purposes such as looking at skin. These heads are easy to damage and expensive. The provision of two heads is bulky and reduces portability.

According to a first aspect of the invention, there is provided a device forming a combination ophthalmoscope and otoscope, having a housing supporting a light source and a plurality of lenses, the light source defining an illumination light path which illuminates in use a region of interest, the housing having an aperture defining a viewing light path along which the region of interest can be viewed, the lenses being mounted on a support relative to the housing so as to be moveable relative to the housing so as to allow selection of a lens from the plurality of lenses to be disposed in the viewing light path, and in which the plurality of lenses form an ophthalmoscopy set comprising at least one ophthalmoscopy lens and an otoscopy set comprising at least one otoscopy lens.

As such, such a device obviates the need to have separate ophthalmoscopes and otoscopes, or separate detachable heads for the same housing.

The support may allow the lenses to rotate relative to the housing; typically the support itself will rotate, with the lenses being fixed relative to the support.

With a lens of the ophthalmoscopy set in the viewing light path, the device will typically be suitable for performing ophthalmoscopy (preferably as a direct ophthalmoscope); typically, the or each lens of the ophthalmoscopy set would allow the user to view the posterior surface of a subject's eye and would accommodate for differing focal lengths of the user's and subject's eyes. As such, the or each lens of the ophthalmoscopy set may have a strength typically between −40 and +40 dioptres. However many ophthalmoscopes have a different ranges of lenses due to size of the head and level of complexity wanted.

With one of the lenses of the otoscopy set in the viewing light path, the device will typically be suitable for performing otoscopy; typically, the or each lens of the otoscopy set would allow the user to see a magnified view of a subject's ear canal, an in particular the tympanic membrane. As such, the or each lens of the otoscopy set may have a strength of at least 2-3 magnification strength or a strength currently required in clinical practice. The or each lens of the otoscopy set may also be larger (that is, wider relative to the optical axis of the lens) than the or each lens of the ophthalmoscopy set. This is because a wider field of vision is desired in the case of otoscopy than in ophthalmoscopy, and is possible as there is no pupil in the ear canal to restrict the field of vision.

The device may have a fitting for supporting an ear speculum, typically a disposable speculum; additionally or alternatively, the device may comprise an ear speculum.

The ear speculum may surround the viewing or illumination light paths, and may act in use to deflect or straighten the ear canal of a subject in order to provide a better view of surfaces of interest. This would not previously have been provided on ophthalmoscopes, given that there would be no need to deflect any body part when viewing a subject's eye.

The device may comprise an illumination shutter, which selectively blocks the illumination light path. Typically, this will allow the size (preferably diameter) of a light beam emitted from the light source to be controlled. As such, the illumination shutter may comprise a variable size aperture or iris provided about the illumination light path.

The device may comprise a viewing shutter, which selectively blocks the viewing light path. Typically, this will allow the field of view of the device to be controlled.

As such, the viewing shutter may comprise a variable size aperture or iris provided about the viewing light path. Typically, the viewing shutter is capable of being completely closed, so as to provide physical protection to the device and in particular the lenses when not in use. This can prevent dust accumulation, which can affect device performance. In addition, a further lens, typically fixed relative to the housing, may be provided, which selectively blocks the viewing light path on the opposite side of the lens that is in the viewing light path to the viewing shutter.

At least one of the illumination and the viewing shutter may be linked to the support, such that the position of the support affects the level to which the shutter obscures its light path. This may allow the device to automatically adjust its shutter settings to accommodate whether the lens in the viewing light path belongs to the ophthalmoscopy or otoscopy sets. For example, when a lens of the otoscopy set is in the viewing light path, the shutters may be fully open; when a lens of the ophthalmoscopy set is in the viewing light path, the shutters may be partially closed.

The support may be of the form of a rotating disc, which would typically carry the lenses spaced circumferentially about the disc. The lenses may be provided in at least one (or more) concentric tracks. Typically, the lenses of the ophthalmoscopy set and of the otoscopy set may be provided on different tracks. Alternatively, where the otoscopy set comprises a single lens, the lens of the otoscopy set may be carried at the centre of the disc, with the lenses of the ophthalmoscopy set carried in at least one circular track thereabout.

In these embodiments, the selection of whether a lens of the ophthalmoscopy or otoscopy sets is in the viewing light path can be made by displacing the support radially, whereas the selection of lenses within a set can be made by rotating the support about its axis.

According to a second aspect of the invention, there is provided use of the apparatus of the first aspect of the invention in ophthalmoscopy or otoscopy. Typically, this will involve selecting the appropriate lens from the corresponding set, presenting the device to the user's eye, and using the device to examine the region of interest.

There now follows, by way of example only, embodiments of the invention, described with reference to the accompanying drawings, in which:

FIG. 1A shows a front elevation of a combination otoscope and ophthalmoscope according to a first embodiment of the invention, in a first position FIG. 1B shows a side elevation of the device of FIG. 1A;

FIGS. 1C and 1D show corresponding views to FIGS. 1A and 1B of the device in a second position;

FIGS. 1A to 1G show a device forming combination otoscope and ophthalmoscope according to a first embodiment of the invention.

Figure 1E:
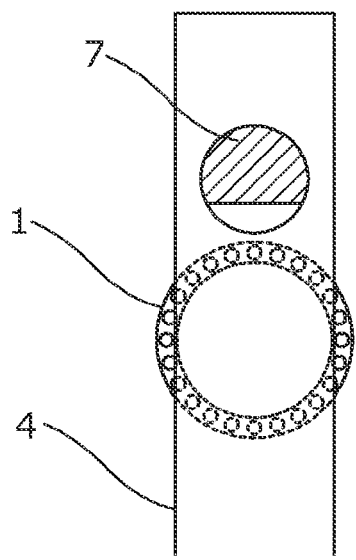
FIGS. 1E and 1F show corresponding views to FIGS. 1A and 1B of the device in a third position.

FIGS. 1A and 1B represents the device being used as an otoscope. The device comprises a housing 4, which supports a light source 10. Matching apertures on the user's side 11 and on the subject's side 12 define a viewing light path 13 along which can be viewed the area of interest 15—here the subject's ear canal. The light emitted from the light source is reflected by a curved mirror 3 to form an illumination light path 14 which illuminates the area of interest 15.

Between the two apertures 11, 12 is held a lens disc 1. This is of the form of a circular disc (shown somewhat schematically at FIG. 1G), which is provided with a single large otoscopy lens 9 of strength approximately +10 Dioptre and diameter 15-20 mm mounted with its optical axis passing through the centre of the disc 1 and perpendicular thereto.

The lens disc 1 is also provided with a plurality of smaller (diameter 4-6 mm) ophthalmoscopy lenses 8 in a circular track surrounding the otoscopy lens 9; the circular track is coaxial with the optical axis of the otoscopy lens and the optical axes of each of the ophthalmoscopy lenses 8 is perpendicular to the lens disc 1. The strength of the ophthalmoscopy lenses varies between X and Y in steps of Z.

The lens disc 1 is mounted between the apertures 11, 12 so that it can rotate about its axis (that is, about the optical axis of the otoscopy lens 9) and displace linearly in a single direction in the plane of the disc 1. This allows the various lenses to be selected by the user.

In the position shown in FIGS. 1A and 1B of the accompanying drawings, the lens disc has been displaced upwards in the sense of FIG. 1A, so that the otoscopy lens 9 is in the viewing light path 13. The apertures 11, 12 are left unobscured. An ear speculum 2 is attached to a bayonet or other click-fastening 16 around the subject-side aperture 12, and can be used to straighten the ear canal 15. The otoscopy lens 9 acts to magnify the view of the area of interest 15—that is the ear canal.

To use the device as an ophthalmoscope, the user presses the lens disc 1 downwards, into the position shown in FIGS. 1C and 1D. Typically, this movement would require significantly more force than the rotational movement of the lens disc 1, so that the user does not unintentionally change modes. This displacement interposes one of the ophthalmoscopy lenses 8 into the viewing light path 13. The ophthalmoscopy lenses are arranged in order of strength, such that by rotating the lens disc about its axis, gradual steps of focus can be made until the user finds the appropriate lens to accommodate for the combination of the visual acuities of both the user and subject.

The user-side aperture 11 is provided with a shutter 6 which automatically constricts when the lens disc 1 is slid down into the ophthalmoscopy position. This is because of the much smaller field of view required and achievable in ophthalmoscopy. A similar shutter can be provided on the subject-side aperture 12, so as to reduce the diameter of the beam generated by the light source 10 to the size required by the user for the particular subject. No speculum is attached, as none is necessary.

Figure 1F:
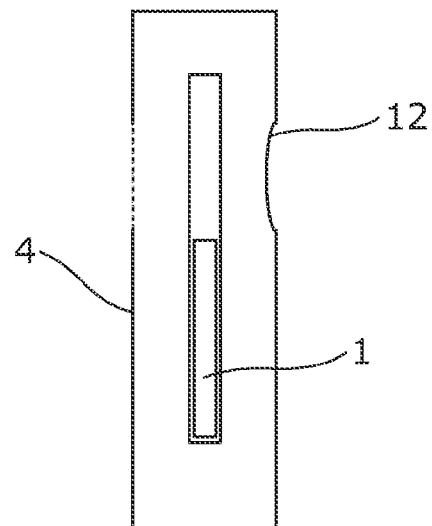
Figure 1G:
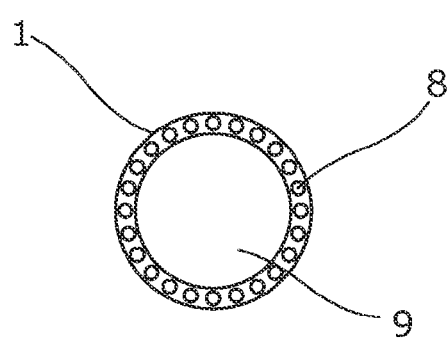
FIG. 1G shows the lens disc of the device of FIG. 1A in more detail.

If the lens disc 1 is pushed further down, to the position shown in FIGS. 1E and 1F of the accompanying drawings, the lenses 8, 9 are removed from the viewing light path 13 and protected from harm. Either the shutter 6 or a separate shutter 7 can automatically close the apertures 11, 12 automatically.

A further, fixed lens 17 can be provided in the subject-side aperture 12 (shown in FIG. 1B only), so as to prevent the ingress of dust or so on into the housing 4. Thus, when the shutter 6 or 7 is closed, both the user- and subject-side apertures will be sealed.

The light source 10 can be a light bulb or LED, or can be external to the housing 4 and transmitted into the housing 4 by fibre optics or other means. Similarly, whilst a mirror 3 has been shown, a fibre optic arrangement can be used to generate the desired beam shape.

Figure 2A:
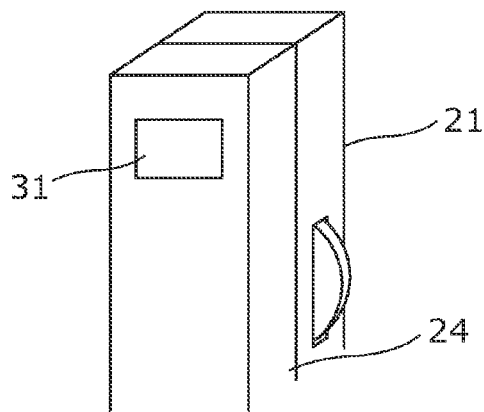
FIG. 2A shows a perspective view of a combination otoscope and ophthalmoscope according to a second embodiment of the invention.
Figure 2B:
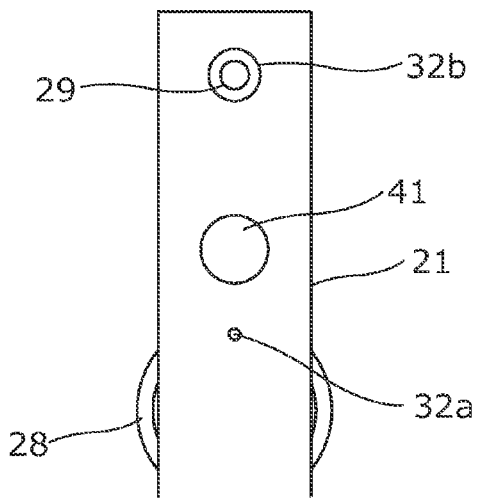
FIG. 2B shows an elevation of the device of FIG. 2A, taken from the opposite side.
Figure 2C:
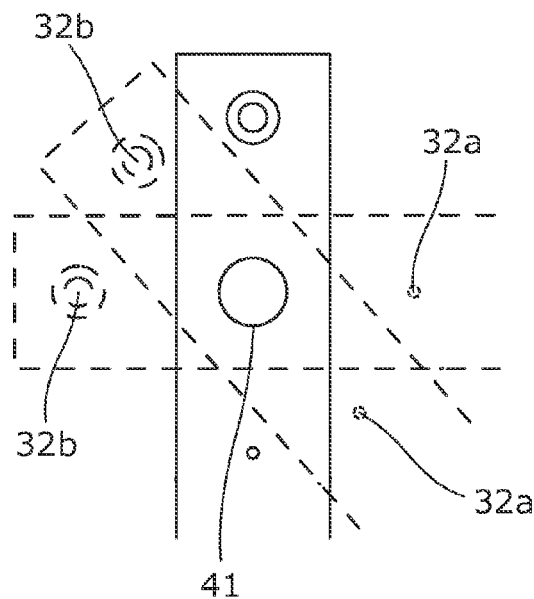
FIG. 2C shows a similar view to that of FIG. 2B, with the device being changed between otoscope and ophthalmoscope modes.

A further combination device forming both an ophthalmoscope and otoscope according to a second embodiment of the invention is shown in FIGS. 2A to 2C of the accompanying drawings. Corresponding integers to those of the first embodiment have been given corresponding reference numerals, raised by 20.

In this embodiment, the light source (not shown) is held within a housing 24, which also carries the user-side aperture 31. Rather than the lens disc of the first embodiment, a rotating arm 21 is provided, which rotates relative to the housing 24 about a pivot 41. The rotating arm 21 contains two sets of lenses; a single otoscopy lens 29 with a corresponding subject aperture 32b, and a plurality of ophthalmoscopy lenses mounted on a lens disc 28, with their corresponding subject-side aperture 32a.

Rotating the rotating arm as shown in FIG. 2C causes the appropriate set of lenses 28, 29 and subject-side aperture 32a, 32b to be aligned with the user-side aperture 31 and so form the viewing light path. There is a locking mechanism (not shown) to hold the rotating arm 21 when it is flush in the desired position with the rest of the housing 24.

In the above embodiments, it has been envisaged that the lens selected is between the light source and the area of illumination. Some prior art otoscopes use a fibre optic light source. In such an arrangement, the otoscope lens comes between the user's eye and the light source. Therefore, in a third embodiment, the otoscope lens can be placed before the source of illumination and being mounted on a support similar to that described for the preceding embodiments, which can be used to selectively interpose the ophthalmoscopy lenses and the otoscopy lens in the viewing but not the illumination light path. In a yet further embodiment, the light source is coupled directly to the selected lens either in the plane of the lens or is part of the lens mounting.

The invention claimed is:

1. A device forming a combination ophthalmoscope and otoscope, having a housing supporting a light source and a plurality of lenses, the light source defining an illumination light path which illuminates in use a region of interest, the housing having an aperture defining a viewing light path along which the region of interest can be viewed, the lenses being mounted on a support relative to the housing so as to be moveable relative to the housing so as to allow selection of a lens from the plurality of lenses to be disposed in the viewing light path, and in which the plurality of lenses form an ophthalmoscopy set comprising at least one ophthalmoscopy lens and an otoscopy set comprising at least one otoscopy lens, further comprising a viewing shutter, which selectively blocks the viewing light path so as to allow the field of view of the device to be controlled.

2. The device of claim 1 in which the support allows the lenses to rotate relative to the housing.

3. The device of claim 2 in which the support rotates relative to the housing, with the lenses being fixed relative to the support.

4. The device of claim 1, in which, with a lens of the ophthalmoscopy set in the viewing light path, the device will be suitable for performing ophthalmoscopy.

5. The device of claim 1, in which, with one of the lenses of the otoscopy set in the viewing light path, the device will be suitable for performing otoscopy.

6. The device of claim 1, in which each lens of the ophthalmoscopy set has a strength between −40 and +40 dioptres.

7. The device of claim 1, in which each lens of the otoscopy set has a strength of at least 2-3 magnification strength.

8. The device of claim 1, in which each lens of the otoscopy set is larger than each lens of the ophthalmoscopy set.

9. The device of claim 1, comprising a fitting for supporting an ear speculum.

10. The device of claim 9, comprising an ear speculum which surrounds at least one of the viewing and illumination light paths.

11. The device of claim 1, comprising an illumination shutter, which selectively blocks the illumination light path so as to allow a size of a light beam emitted from the light source to be controlled.

12. The device of claim 11 in which the illumination shutter is linked to the support, such that the position of the support affects the level to which the illumination shutter obscures the illumination light path.

13. The device of claim 1, in which the viewing shutter is capable of being completely closed.

14. The device of claim 1, in which the lenses are mounted relative to the housing by the support such that a first selection of whether a lens of the ophthalmoscopy or otoscopy sets is in the viewing light path is made by displacing the support radially, whereas the a second selection which lens within a set is in the viewing light path is made by rotating the support about its axis.

15. The device of claim 1, in which the viewing shutter is linked to the support, such that the position of the support affects the level to which the viewing shutter obscures the viewing light path.

16. A method of carrying out ophthalmoscopy and otoscopy, comprising:
providing a device forming a combination ophthalmoscope and otoscope, having a housing supporting a light source and a plurality of lenses, the light source defining an illumination light path which illuminates in use a region of interest, the housing having an aperture defining a viewing light path along which the region of interest can be viewed, the lenses being mounted on a support relative to the housing so as to be moveable relative to the housing so as to allow selection of a lens from the plurality of lenses to be disposed in the viewing light path, and in which the plurality of lenses form an ophthalmoscopy set comprising at least one ophthalmoscopy lens and an otoscopy set comprising at least one otoscopy lens, further comprising a viewing shutter, which selectively blocks the viewing light path so as to allow the field of view of the device to be controlled; and
using the device to view a region of interest in a patient's eye and a region of interest in a patient's ear canal.

17. The method of claim 16, comprising selecting an appropriate lens from the set corresponding to whether ophthalmoscopy or otoscopy is being carried out, presenting the device to the user's eye or ear, and using the device to examine the region of interest.

18. A device forming a combination ophthalmoscope and otoscope, having a housing supporting a light source and a plurality of lenses, the light source defining an illumination light path which illuminates in use a region of interest, the housing having an aperture defining a viewing light path along which the region of interest can be viewed, the lenses being mounted on a support relative to the housing so as to be moveable relative to the housing so as to allow selection of a lens from the plurality of lenses to be disposed in the viewing light path, and in which the plurality of lenses form an ophthalmoscopy set comprising at least one ophthalmoscopy lens and an otoscopy set comprising at least one otoscopy lens, in which the lenses are mounted relative to the housing by the support such that a first selection of whether a lens of the ophthalmoscopy or otoscopy sets is in the viewing light path is made by displacing the support radially, whereas the a second selection of which lens within a set is in the viewing light path is made by rotating the support about its axis.

19. The device of claim 18, comprising a viewing shutter, which selectively blocks the viewing light path so as to allow a field of view of the device to be controlled.

* * * * *